(12) United States Patent
MacMeans et al.

(10) Patent No.: US 8,747,343 B2
(45) Date of Patent: Jun. 10, 2014

(54) HEMODIALYSIS CATHETER WITH IMPROVED SIDE OPENING DESIGN

(75) Inventors: Scott MacMeans, Wrentham, MA (US); Michael R. Sansoucy, Wrentham, MA (US); Gaurav Girdhar, North Attleboro, MA (US); Richard M. Braga, North Easton, MA (US)

(73) Assignee: Covidien LP, Mansfield, MA (US)

( * ) Notice: Subject to any disclaimer, the term of this patent is extended or adjusted under 35 U.S.C. 154(b) by 33 days.

(21) Appl. No.: 13/250,112

(22) Filed: Sep. 30, 2011

(65) Prior Publication Data

US 2013/0085438 A1 Apr. 4, 2013

(51) Int. Cl.
*A61M 25/00* (2006.01)

(52) U.S. Cl.
CPC .......... *A61M 25/00* (2013.01); *A61M 25/0029* (2013.01); *A61M 25/0015* (2013.01)
USPC ........................................ 604/6.16; 604/264

(58) Field of Classification Search
CPC ... A61M 25/00; A61M 1/36; A61M 25/0015; A61M 25/0026; A61M 25/0029; A61M 5/329; A61M 5/3291
USPC .............. 604/6.16, 264, 266, 102.01, 102.02, 604/102.03
See application file for complete search history.

(56) References Cited

U.S. PATENT DOCUMENTS

| 701,075 | A | 5/1902 | McCully |
| 2,541,691 | A | 2/1951 | Eicher |
| D208,838 | S | 10/1967 | St. Amand |
| 4,134,402 | A | 1/1979 | Mahurkar |
| D254,270 | S | 2/1980 | Ziegler |
| 4,391,276 | A | 7/1983 | Lazarus et al. |
| 4,403,983 | A | 9/1983 | Edelman et al. |
| D272,651 | S | 2/1984 | Mahurkar |
| 4,443,333 | A | 4/1984 | Mahurkar |
| 4,493,696 | A | 1/1985 | Uldall |
| 4,568,329 | A | 2/1986 | Mahurkar |
| 4,583,968 | A | 4/1986 | Mahurkar |

(Continued)

FOREIGN PATENT DOCUMENTS

| CA | 2 326 941 | 10/1976 |
| CA | 2 389 227 | 10/2001 |

(Continued)

OTHER PUBLICATIONS

Bard Access Systems Power-Trialysis Short-Term Dialysis Catheter—Short-Term Triple Lumen Dialysis Catheter, Enhanced Acute Dialysis Care.

(Continued)

*Primary Examiner* — Philip R Wiest
*Assistant Examiner* — Benjamin Klein
(74) *Attorney, Agent, or Firm* — John Paul Mello, Esq.

(57) ABSTRACT

A hemodialysis catheter is provided which includes a catheter body having a proximal and a distal end and defining at least one lumen. The at least one lumen includes a distal opening and a side opening formed through a sidewall of the catheter body. The side opening communicates with the at least one lumen, and includes guiding structure positioned adjacent a distal side of the side opening configured to smoothly redirect blood flow into the at least one lumen. The guiding structure may be defined by a raised wall, or in the alternative, an angled distal wall of the side opening.

5 Claims, 5 Drawing Sheets

(56) References Cited

U.S. PATENT DOCUMENTS

| | | |
|---|---|---|
| 4,601,697 A | 7/1986 | Mammolenti et al. |
| 4,604,379 A | 8/1986 | Twardowski et al. |
| 4,619,643 A | 10/1986 | Bai |
| 4,626,240 A | 12/1986 | Edelman et al. |
| 4,643,711 A | 2/1987 | Bates |
| D289,682 S | 5/1987 | Dragan |
| 4,675,004 A | 6/1987 | Hadford et al. |
| 4,682,978 A | 7/1987 | Martin |
| 4,687,471 A | 8/1987 | Twardowski et al. |
| 4,692,141 A | 9/1987 | Mahurkar |
| D292,825 S | 11/1987 | Dragan |
| 4,769,005 A | 9/1988 | Ginsburg et al. |
| 4,770,652 A | 9/1988 | Mahurkar |
| 4,772,268 A | 9/1988 | Bates |
| 4,772,269 A | 9/1988 | Twardowski et al. |
| D298,461 S | 11/1988 | Manno |
| 4,795,439 A | 1/1989 | Guest |
| 4,808,155 A | 2/1989 | Mahurkar |
| 4,808,156 A | 2/1989 | Dean |
| 4,842,582 A | 6/1989 | Mahurkar |
| 4,894,057 A | 1/1990 | Howes |
| 4,895,561 A | 1/1990 | Mahurkar |
| 4,897,079 A | 1/1990 | Zaleski et al. |
| 4,904,238 A | 2/1990 | Williams |
| 4,961,809 A | 10/1990 | Martin |
| D312,872 S | 12/1990 | Mähl |
| 4,995,865 A | 2/1991 | Gahara et al. |
| 5,009,636 A | 4/1991 | Wortley et al. |
| 5,015,184 A | 5/1991 | Perry et al. |
| 5,035,399 A | 7/1991 | Rantanen-Lee |
| 5,041,083 A | 8/1991 | Tsuchida et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,085,632 A | 2/1992 | Ikada et al. |
| 5,106,368 A | 4/1992 | Uldall et al. |
| 5,135,599 A | 8/1992 | Martin et al. |
| 5,156,592 A | 10/1992 | Martin et al. |
| 5,167,623 A | 12/1992 | Cianci et al. |
| 5,171,218 A | 12/1992 | Fonger et al. |
| 5,171,227 A | 12/1992 | Twardowski et al. |
| 5,188,593 A | 2/1993 | Martin |
| 5,190,520 A | 3/1993 | Fenton, Jr. et al. |
| 5,195,962 A | 3/1993 | Martin et al. |
| 5,197,951 A | 3/1993 | Mahurkar |
| 5,209,723 A | 5/1993 | Twardowski et al. |
| 5,219,335 A | 6/1993 | Willard et al. |
| 5,221,255 A | 6/1993 | Mahurkar et al. |
| 5,221,256 A | 6/1993 | Mahurkar |
| 5,224,938 A * | 7/1993 | Fenton, Jr. .................. 604/247 |
| 5,273,527 A | 12/1993 | Schatz et al. |
| 5,281,134 A | 1/1994 | Schultz |
| 5,282,788 A | 2/1994 | Wilk et al. |
| 5,290,282 A | 3/1994 | Casscells |
| 5,308,338 A | 5/1994 | Helfrich |
| 5,318,518 A | 6/1994 | Piechinger et al. |
| 5,336,165 A | 8/1994 | Twardowski |
| 5,346,471 A | 9/1994 | Raulerson |
| 5,348,536 A | 9/1994 | Young et al. |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,395,316 A | 3/1995 | Martin |
| 5,403,291 A | 4/1995 | Abrahamson |
| 5,405,341 A | 4/1995 | Martin |
| 5,419,777 A | 5/1995 | Hofling |
| 5,451,206 A | 9/1995 | Young |
| 5,451,216 A | 9/1995 | Quinn |
| 5,464,398 A | 11/1995 | Haindl |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,536,234 A | 7/1996 | Newman |
| 5,549,541 A | 8/1996 | Muller |
| 5,554,136 A | 9/1996 | Luther |
| 5,556,390 A | 9/1996 | Hicks |
| 5,562,640 A | 10/1996 | McCabe et al. |
| 5,569,182 A | 10/1996 | Twardowski et al. |
| 5,571,093 A | 11/1996 | Cruz et al. |
| 5,607,440 A | 3/1997 | Danks et al. |
| D381,420 S | 7/1997 | Musgrave et al. |
| D384,411 S | 9/1997 | Musgrave et al. |
| D384,741 S | 10/1997 | Musgrave et al. |
| 5,683,640 A | 11/1997 | Miller et al. |
| 5,685,867 A | 11/1997 | Twardowski et al. |
| 5,702,365 A | 12/1997 | King |
| 5,707,351 A | 1/1998 | Dorsey, III |
| 5,718,678 A | 2/1998 | Fleming, III |
| 5,725,495 A | 3/1998 | Strukel et al. |
| 5,776,092 A | 7/1998 | Farin et al. |
| 5,776,096 A | 7/1998 | Fields |
| 5,782,797 A | 7/1998 | Schweich, Jr. et al. |
| 5,785,678 A | 7/1998 | Griep et al. |
| 5,788,680 A | 8/1998 | Linder |
| 5,788,681 A | 8/1998 | Weaver et al. |
| 5,797,869 A | 8/1998 | Martin et al. |
| 5,801,012 A | 9/1998 | Soff et al. |
| 5,807,311 A | 9/1998 | Palestrant |
| 5,807,329 A | 9/1998 | Gelman |
| 5,810,789 A | 9/1998 | Powers et al. |
| 5,830,184 A | 11/1998 | Basta |
| 5,830,196 A | 11/1998 | Hicks |
| 5,858,009 A | 1/1999 | Jonkman |
| 5,868,717 A | 2/1999 | Prosl |
| 5,902,476 A | 5/1999 | Twardowski |
| 5,947,953 A | 9/1999 | Ash et al. |
| 5,961,485 A | 10/1999 | Martin |
| 5,961,486 A | 10/1999 | Twardowski et al. |
| 5,976,103 A | 11/1999 | Martin |
| 5,989,206 A | 11/1999 | Prosl et al. |
| 5,989,213 A | 11/1999 | Maginot |
| 5,993,437 A | 11/1999 | Raoz |
| 6,001,079 A | 12/1999 | Pourchez |
| 6,004,310 A | 12/1999 | Bardsley et al. |
| 6,063,099 A | 5/2000 | Danks et al. |
| 6,086,565 A | 7/2000 | Ouchi |
| 6,099,519 A | 8/2000 | Olsen et al. |
| 6,123,725 A | 9/2000 | Aboul-Hosn |
| 6,126,631 A | 10/2000 | Loggie |
| 6,132,616 A | 10/2000 | Twardowski et al. |
| 6,146,354 A | 11/2000 | Beil |
| 6,146,536 A | 11/2000 | Twardowski |
| 6,152,910 A | 11/2000 | Agro et al. |
| 6,156,016 A | 12/2000 | Maginot |
| 6,190,349 B1 | 2/2001 | Ash et al. |
| 6,190,357 B1 | 2/2001 | Ferrari et al. |
| 6,190,371 B1 | 2/2001 | Maginot et al. |
| 6,206,849 B1 | 3/2001 | Martin et al. |
| 6,273,875 B1 | 8/2001 | Siman et al. |
| 6,280,423 B1 | 8/2001 | Davey et al. |
| 6,293,927 B1 | 9/2001 | McGuckin, Jr. |
| 6,299,444 B1 | 10/2001 | Cohen |
| 6,342,120 B1 | 1/2002 | Basta |
| 6,346,090 B1 | 2/2002 | Liska et al. |
| 6,394,141 B2 | 5/2002 | Wages et al. |
| 6,409,700 B1 | 6/2002 | Siegel, Jr. et al. |
| 6,423,050 B1 | 7/2002 | Twardowski |
| 6,428,502 B1 | 8/2002 | Lang |
| 6,447,488 B2 | 9/2002 | Estabrook et al. |
| 6,461,321 B1 | 10/2002 | Quinn |
| 6,475,207 B1 | 11/2002 | Maginot et al. |
| 6,482,169 B1 | 11/2002 | Kuhle |
| 6,506,182 B2 | 1/2003 | Estabrook et al. |
| 6,517,529 B1 * | 2/2003 | Quinn .......................... 604/528 |
| 6,540,714 B1 * | 4/2003 | Quinn ............................ 604/43 |
| 6,576,609 B1 | 6/2003 | Soff et al. |
| 6,579,261 B1 | 6/2003 | Kawamura |
| 6,585,705 B1 | 7/2003 | Maginot et al. |
| 6,592,542 B2 | 7/2003 | Childers et al. |

(56) References Cited

U.S. PATENT DOCUMENTS

| | | |
|---|---|---|
| 6,592,558 B2 | 7/2003 | Quah |
| 6,592,565 B2 | 7/2003 | Twardowski |
| 6,595,966 B2 | 7/2003 | Davey et al. |
| 6,620,118 B1 | 9/2003 | Prosl et al. |
| 6,638,242 B2 | 10/2003 | Wilson et al. |
| 6,692,473 B2 | 2/2004 | St. Cyr et al. |
| 6,695,832 B2 | 2/2004 | Schon et al. |
| 6,719,749 B1 | 4/2004 | Schweikert et al. |
| 6,723,084 B1 | 4/2004 | Maginot et al. |
| 6,730,096 B2 | 5/2004 | Basta |
| 6,743,218 B2 | 6/2004 | Maginot et al. |
| 6,749,580 B2 | 6/2004 | Work et al. |
| 6,758,836 B2 | 7/2004 | Zawacki |
| 6,786,884 B1 | 9/2004 | DeCant, Jr. et al. |
| 6,808,510 B1 | 10/2004 | DiFiore |
| 6,814,718 B2 | 11/2004 | McGuckin, Jr. et al. |
| 6,858,019 B2 | 2/2005 | McGuckin, Jr. et al. |
| 6,872,198 B1 | 3/2005 | Wilson et al. |
| 6,911,014 B2 | 6/2005 | Wentling et al. |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,966,886 B2 | 11/2005 | Appling |
| 6,969,381 B2 | 11/2005 | Voorhees |
| 6,976,973 B1 | 12/2005 | Ruddell et al. |
| 6,986,752 B2 | 1/2006 | McGuckin, Jr. et al. |
| 6,991,625 B1 | 1/2006 | Gately et al. |
| 7,008,395 B1 | 3/2006 | Loggie |
| 7,008,412 B2 | 3/2006 | Maginot |
| 7,011,645 B2 | 3/2006 | McGuckin, Jr. et al. |
| 7,013,928 B2 | 3/2006 | Navis |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,141,035 B2 | 11/2006 | Haggstrom |
| 7,223,263 B1 | 5/2007 | Seno |
| 7,322,953 B2 | 1/2008 | Redinger |
| 7,569,029 B2 | 8/2009 | Clark |
| 2002/0121282 A1 | 9/2002 | McGuckin |
| 2003/0032918 A1 | 2/2003 | Quinn |
| 2003/0093029 A1 | 5/2003 | McGuckin, Jr. et al. |
| 2003/0191425 A1 | 10/2003 | Rosenblatt |
| 2004/0167463 A1 | 8/2004 | Zawacki et al. |
| 2004/0249337 A1 | 12/2004 | DiFiore |
| 2005/0033222 A1 | 2/2005 | Haggstrom et al. |
| 2005/0085765 A1 | 4/2005 | Voorhees |
| 2005/0090776 A1 | 4/2005 | McGuckin, Jr. et al. |
| 2005/0177094 A1 | 8/2005 | Igarashi et al. |
| 2005/0215978 A1 | 9/2005 | Ash |
| 2005/0228339 A1 | 10/2005 | Clark |
| 2005/0267400 A1 | 12/2005 | Haarala et al. |
| 2005/0288623 A1 | 12/2005 | Hjalmarsson |
| 2006/0004325 A1 | 1/2006 | Hamatake et al. |
| 2007/0100298 A1 | 5/2007 | Appling |
| 2008/0082080 A1 | 4/2008 | Braga |
| 2009/0054825 A1* | 2/2009 | Melsheimer et al. ........ 604/6.16 |
| 2009/0192435 A1* | 7/2009 | Gregersen .................... 604/6.16 |
| 2010/0069818 A1 | 3/2010 | Smouse |
| 2010/0076404 A1 | 3/2010 | Ring |
| 2010/0081986 A1 | 4/2010 | Matson et al. |
| 2010/0228230 A1* | 9/2010 | Gately et al. ................. 604/528 |
| 2011/0077577 A1 | 3/2011 | Sansoucy |
| 2011/0130745 A1* | 6/2011 | Shevgoor et al. ............. 604/523 |

FOREIGN PATENT DOCUMENTS

| | | |
|---|---|---|
| EP | 0107810 | 5/1984 |
| EP | 0 299 622 | 1/1989 |
| EP | 0 341 721 | 11/1989 |
| EP | 0 554 722 | 8/1993 |
| EP | 0 623 356 | 11/1994 |
| EP | 0 322 225 | 2/1995 |
| EP | 0 713 406 | 3/1998 |
| EP | 0 570 530 | 8/1999 |
| EP | 0 555 780 | 9/1999 |
| EP | 1 144 039 | 12/2005 |
| EP | 1905476 A2 | 4/2008 |
| EP | 2 168 625 | 3/2010 |
| FR | 2 326 941 | 10/1976 |
| GB | 2028136 | 3/1980 |
| JP | 08103492 | 4/1996 |
| JP | 8308933 | 11/1996 |
| JP | 2004-174130 A | 6/2004 |
| WO | WO 92/14500 | 9/1992 |
| WO | WO 95/04567 | 2/1995 |
| WO | WO 95/10317 | 4/1995 |
| WO | WO 97/37699 | 10/1997 |
| WO | WO 98/41277 | 9/1998 |
| WO | WO 99/38550 | 8/1999 |
| WO | WO 99/65557 | 12/1999 |
| WO | WO 01/91845 | 12/2001 |
| WO | WO 02/13899 | 2/2002 |
| WO | WO 02/18004 | 3/2002 |
| WO | WO 03/033049 | 4/2003 |
| WO | WO 03/066148 | 8/2003 |
| WO | WO 2004/093956 | 11/2004 |
| WO | WO 2005/023336 | 3/2005 |
| WO | WO 2005/077449 | 8/2005 |
| WO | WO 2005/084741 | 9/2005 |
| WO | WO 2006/014339 | 2/2006 |
| WO | 2008155145 A1 | 12/2008 |

OTHER PUBLICATIONS

European Search Report dated Nov. 5, 2012 in copending European Application No. 12 18 4656.
Office Action issued in the corresponding Japanese Application No. 2012-212145 mailed Aug. 28, 2013.
Examiner's Report issued in Australian Appl. No. 2010226891 dated Sep. 5, 2013.
Official Action issued in the corresponding Japanese Appl. No. 2012-214681 dated Aug. 28, 2013.

* cited by examiner

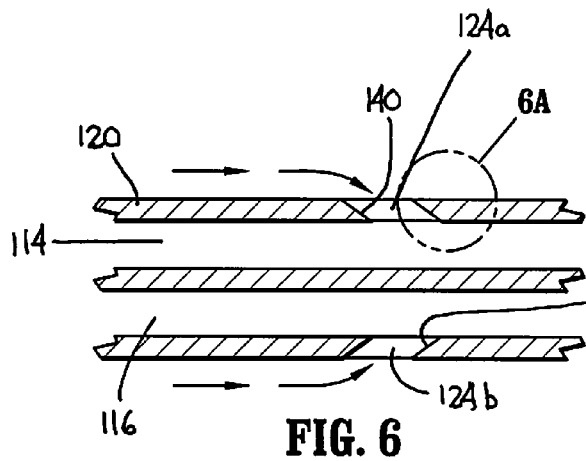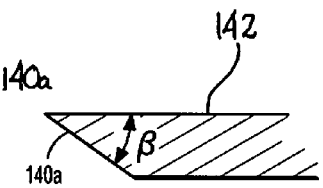
FIG. 6  FIG. 6A
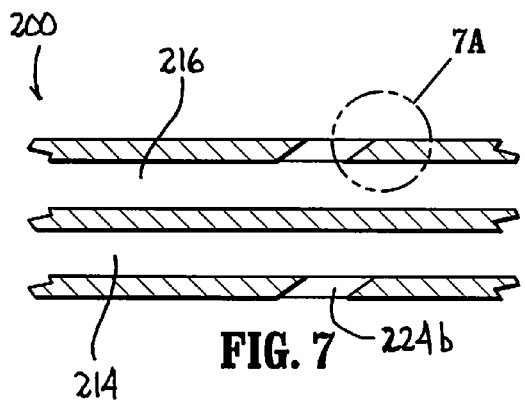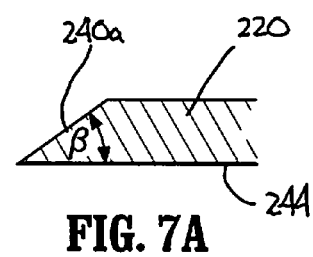
FIG. 7  FIG. 7A
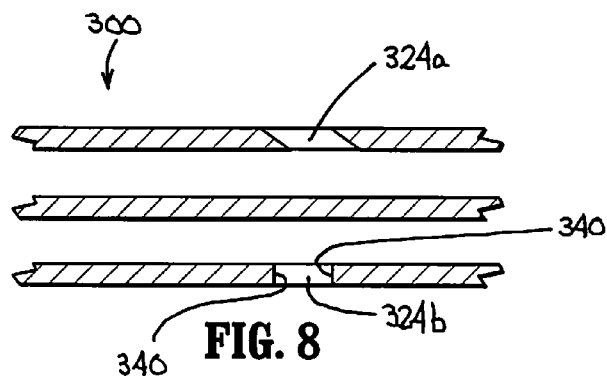
FIG. 8

HEMODIALYSIS CATHETER WITH IMPROVED SIDE OPENING DESIGN

TECHNICAL FIELD

The present disclosure relates to hemodialysis catheters, and in particular, to hemodialysis catheters with improved side openings.

BACKGROUND

Catheters are flexible medical instruments for use in the introduction and withdrawal of fluids to and from body cavities, ducts and vessels. Catheters are used for many different applications within the human body including the administration of liquid therapeutic agents and the removal of bodily fluids for testing, monitoring, or disposal. Catheters have a particular application in hemodialysis procedures, in which blood is withdrawn from a blood vessel, directed to a hemodialysis unit for dialysis or purification, and subsequently returned to the blood vessel.

Typically, dialysis catheters define at least two lumens including a venous lumen and an arterial lumen. The arterial lumen withdraws blood from the patient and delivers the blood to a dialyzer. The venous lumen receives purified blood from the dialyzer and returns the blood to the patient. The venous and arterial lumens may include distal openings adjacent to the tip of the catheter. In addition, the venous and arterial lumens may also include side openings proximal to the tip of the catheter which provide redundant flow paths to and from the arterial and venous lumens.

One problem associated with known dialysis catheters is the susceptibility of known catheters to the formation of thrombus within the openings of the catheter. Thrombus is a clot which consists of fibrin, platelets, red blood cells and white blood cells that form in the lumen of the catheter. The formation of thrombus adjacent to the side openings of the catheter may result in occlusion of the side openings of the catheter and obstruct, partially or completely, blood flow to or from the catheter. The likelihood of thrombus formation is increased by disruptive blood flow which results in elevated shear stress on the blood.

It would be desirable to provide a catheter having side openings which are configured to improve the flow dynamics of the blood flow into the hemodialysis catheter to minimize the formation of thrombus.

SUMMARY

A hemodialysis catheter in accordance with the present disclosure includes a catheter body having a proximal end and a distal end and defining a venous lumen and an arterial lumen. The venous lumen and the arterial lumen each may include a distal opening and a side opening formed through a sidewall of the catheter body. Each distal opening and side opening communicates with a respective venous or arterial lumen. In one embodiment, the hemodialysis catheter includes a guiding structure positioned adjacent to a distal side of the side opening communicating with the arterial lumen. The guiding structure is configured to smoothly redirect blood flow into the arterial lumen through the arterial lumen side opening.

In one embodiment, the guiding structure includes a raised wall positioned adjacent to the distal side of the side opening. The raised wall may define a scoop which extends at least partially over the distal end of the side opening. The scoop may include a radiused proximal surface configured to smoothly redirect blood flow into the arterial lumen of the catheter.

In one embodiment, the height "h" of the scoop extends above the exterior surface of the sidewall of the catheter between about "t" and about 3 t, wherein "t" is the thickness of the sidewall of the catheter. In one embodiment, h is about 1.5 t.

In another embodiment, the guiding structure includes an angled distal inner wall which defines the side opening. The angled distal inner wall defines an acute angle β adjacent to the exterior surface of the sidewall of the catheter.

In one embodiment, β is between about 15 degrees and about 75 degrees. In another embodiment, β is about 45 degrees.

In one embodiment, guiding structure is formed adjacent to the distal end of the side opening that communicates with the venous lumen.

In one embodiment, the hemodialysis catheter is reversible and the guiding structure formed adjacent to the distal end of the side opening that communicates with the venous lumen defines the acute angle β with the exterior surface of the sidewall of the catheter wherein β is between about 15 degrees and 75 degrees. In another embodiment, β is about 45 degrees.

In one embodiment, the side opening that communicates with the venous lumen is defined by walls which are substantially perpendicular to the exterior surface of the catheter.

In one embodiment, the hemodialysis catheter is non-reversible and the guiding structure formed adjacent to the distal end of the side opening that communicates with the venous lumen includes an angled distal inner wall which defines the acute angle β with the interior surface of the catheter.

In one embodiment, a catheter for withdrawing fluid from a patient includes a catheter body defining a first lumen having a side opening spaced from a distal end of the catheter body that communicates with the first lumen. The catheter body includes a guiding structure positioned adjacent to a distal end of the side opening which is configured to smoothly redirect fluid flow into the first lumen through the side opening.

In one embodiment, the guiding structure includes a raised wall positioned adjacent to the distal end of the side opening. The raised wall may define a scoop which includes a radiused proximally facing surface.

In another embodiment, the guiding structure includes an angled distal inner wall defining the side opening which defines an angle β with the exterior surface of the catheter body, wherein β is between about 15 degrees and about 75 degrees. In another embodiment, β is between about 30 degrees and about 60 degrees.

BRIEF DESCRIPTION OF THE DRAWINGS

FIG. 6 is a cross-sectional view taken along section lines 6-6 of FIG. 5;

FIG. 6A is an enlarged view of the indicated area of detail shown in FIG. 6;

FIG. 7 is a side cross-sectional view of an alternate embodiment of the presently disclosed hemodialysis catheter;

FIG. 7A is an enlarged view of the indicated area of detail shown in FIG. 7; and FIG. 8 is a side cross-sectional view of another alternate embodiment of the presently disclosed hemodialysis catheter.

DETAILED DESCRIPTION OF EMBODIMENTS

Various exemplary embodiments of the presently disclosed hemodialysis catheter are discussed herein. It is envisioned that the principles of the present disclosure are equally applicable to a range of other known catheter applications such as, for example, cardiac, abdominal, urinary, and intestinal catheters, for both chronic and acute applications.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human patient or other animal, and the term "clinician" should be understood as referring to a doctor, nurse or other care provider and may include support personnel.

Figure 1:
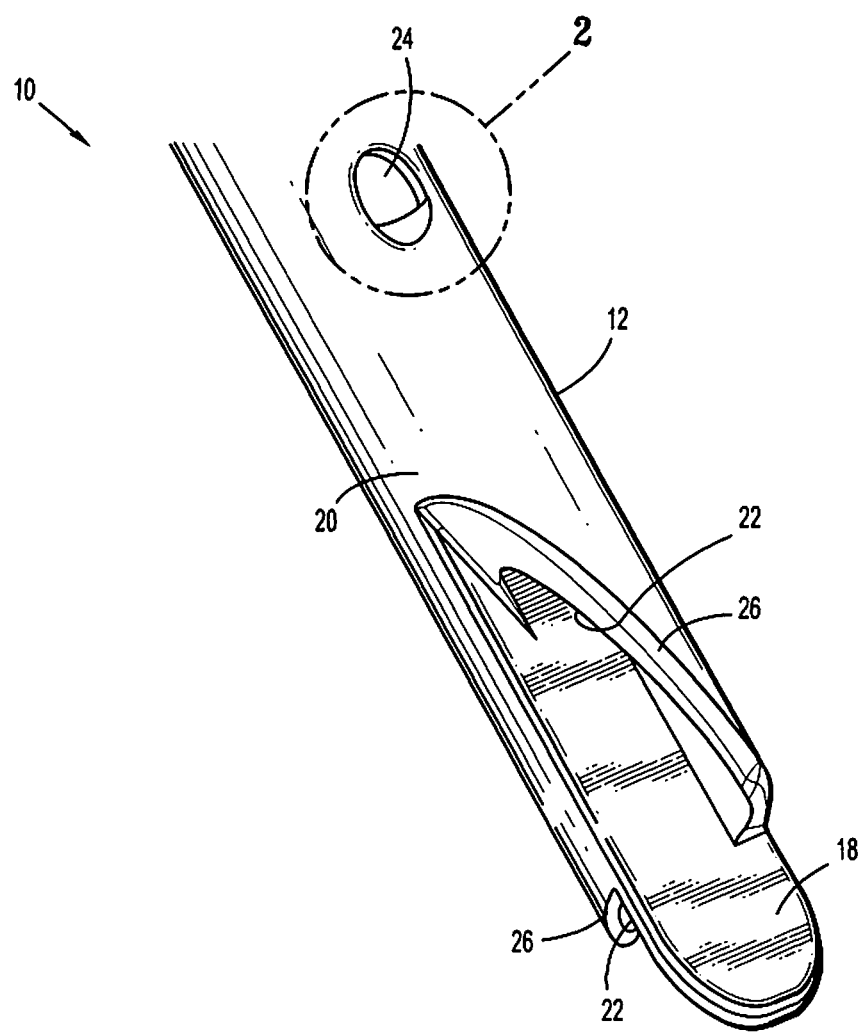
FIG. 1 is a side perspective view of the distal end of one embodiment of the presently disclosed hemodialysis catheter.
Figure 2:
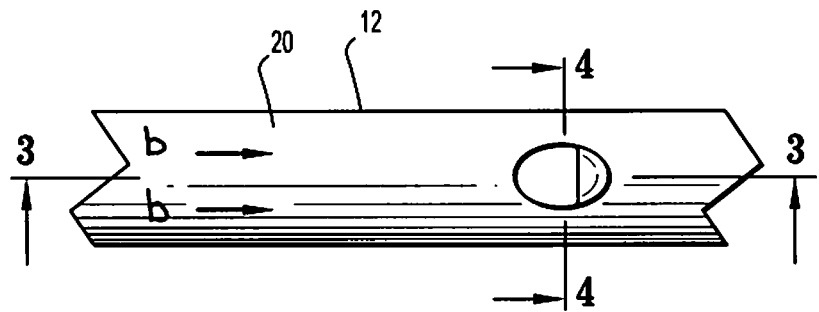
FIG. 2 is an enlarged view of the indicated area of detail shown in FIG. 1.
Figure 3:
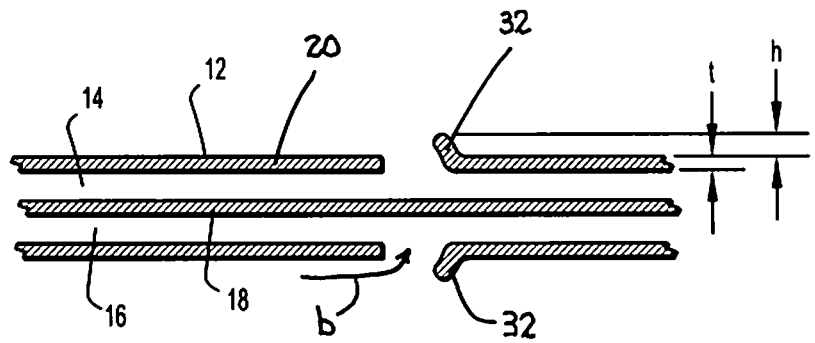
FIG. 3 is a cross-sectional view taken along section lines 3-3 of FIG. 2.
Figure 4:
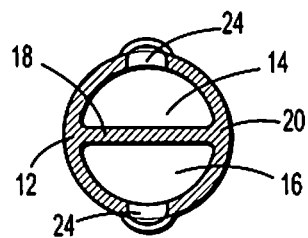
FIG. 4 is a cross-sectional view taken along section lines 4-4 of FIG. 2.

FIGS. 1-4 illustrate one exemplary embodiment of the presently disclosed catheter shown generally as 10. Catheter 10 includes a catheter body 12 defining a first lumen 14 and a second lumen 16 (FIG. 4). As illustrated, first and second lumens 14 and 16 are substantially D-shaped. Alternately, it is envisioned that lumens 14 and 16 may have a variety of configurations including circular, oval, etc. A septum 18 extends from the proximal end of the body 10 to the distal end of body 10. In one embodiment, the septum 18 extends distally of a distal end of the sidewalls 20 defining the outer perimeter of body 10.

Catheter body 12 defines a pair of distal openings 22 and a pair of diametrically opposed side openings 24 which are spaced proximally of the distal openings 22. In one embodiment, each distal opening 22 is defined between septum 18 and distal spirally configured sidewall extension 26 of sidewalls 20. A catheter including similarly configured distal sidewall extensions 26 is disclosed in U.S. Pat. No. 7,776,005 which is incorporated herein by reference in its entirety. Alternately, it is envisioned that the distal end of the catheter 10 may assume a variety of configurations known in the art.

Side openings 24 are formed through sidewalls 20 of catheter body 12 at location spaced proximally of distal openings 22. Each opening 24 communicates with one of the first and second lumens 14 and 16. As illustrated, openings 24 are positioned in diametrically opposed locations on body 10. However, it is envisioned that openings 24 can be positioned in any position on lumens 14 and 16; and further in plurality as well. Although openings 24 are illustrated as having an oval configuration, other configurations including polygonal, rectangular, square, trapezoidal, circular, and other regular and irregular shaped openings are envisioned.

As shown in FIG. 1-4, the distal wall of each side openings 24 includes guiding structure for smoothly redirecting blood flow into a respective lumen 14, 16 of the catheter 10. In one embodiment, this structure includes a raised scoop 32 which is formed along the distal end of each side opening 24. The scoop 32 includes a proximal surface which is configured to smoothly redirect fluid flow, identified by arrow "b" in FIG. 3, into the lumen 14 of the catheter 10. More specifically, the proximal wall of scoop 32 is radiused to effect the smooth redirection of fluid flow into the catheter 10. In the illustrated embodiment, the scoop 32 extends over the distal end of each side opening 24. Alternatively, other scoop configurations are envisioned.

In one embodiment, the scoop 32 extends outwardly from an outer surface of sidewall 20 a height "h" at least as great as the thickness "t" of sidewall 20 (FIG. 3). In other embodiments, the height "h" of scoop 32 is between about "t" and about 3 t, and may be about 1.5 t.

Figure 4A:
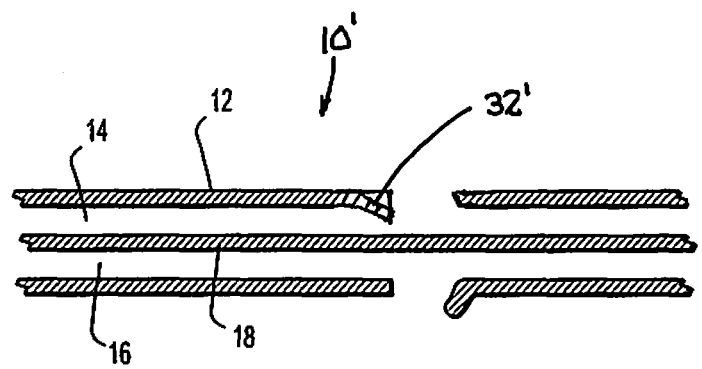
FIG. 4A is a cross-sectional view of another embodiment of the presently disclosed hemodialysis catheter.

As shown in FIG. 4A, a scoop 32' may also be positioned within the catheter 10' on the proximal side of side opening. More specifically, an inwardly extending scoop 32' having a distally facing guide surface may be positioned in lumen 14 to smoothly redirect fluid exiting the lumen 14.

As discussed above, a dual lumen hemodialysis catheter 10 includes an arterial lumen for withdrawing blood from a vein of a patient and a venous lumen for returning purified blood to the vein of a patient. A catheter is classified as a reversible lumen catheter if it is configured such that either lumen of the dual lumen catheter can function as the arterial lumen and the venous lumen. The advantages of reversible lumen catheters, such as the ability to resolve positional occlusions of blood flow through a catheter, are known in the art and are not discussed in detail herein. However, a raised scoop 32 adjacent the side openings may also help alleviate positional occlusion by side wall 20 away from the vessel wall.

Catheter 10, as illustrated, is a reversible lumen catheter, and as such, includes scoops 32 positioned adjacent to the distal end of each side opening 32. It is envisioned that scoop 32 could be incorporated into non-reversible lumen catheters as well as reversible lumen catheters. As such, it is also envisioned that a scoop 32 need only be positioned adjacent the distal end of the side opening 32 which communicates with the arterial lumen 14. Thus, a catheter may include only a single scoop 32.

As discussed above, providing a scoop 32 or similar structure for smoothly redirecting blood flow from a vein into the arterial lumen 14 of a catheter 10, reduces flow disruption and prevents the blood from being exposed to elevated shear stresses for exposure times. By minimizing the exposure of blood flow to elevated shear stress, blood platelet activation is minimized resulting in a reduced likelihood of thrombus formation.

Figure 5:
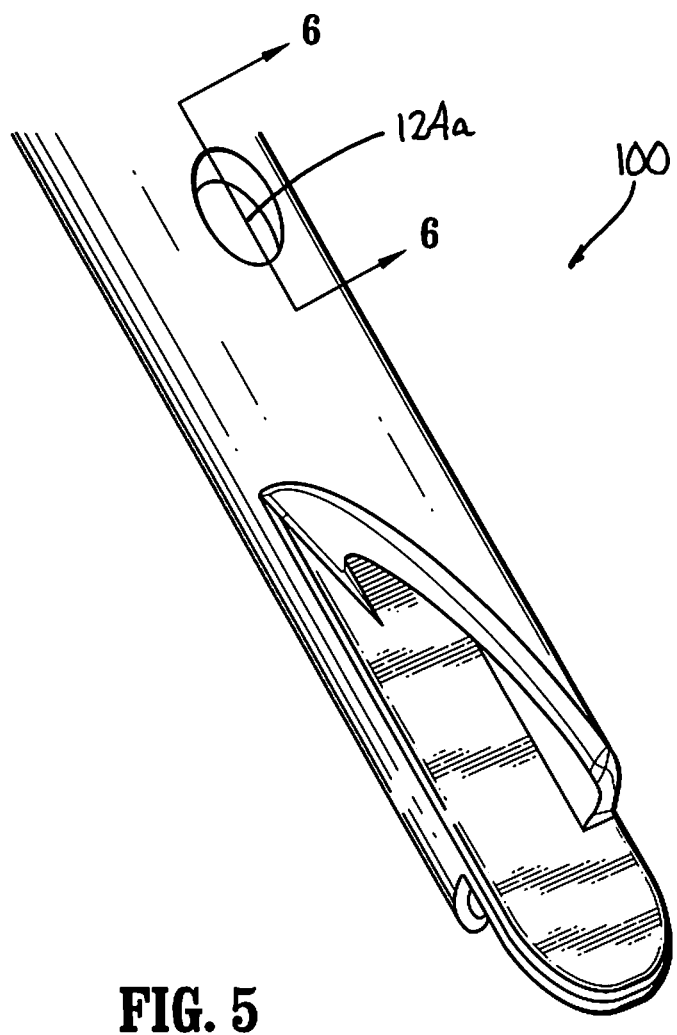
FIG. 5 is a side perspective view of the distal end of another embodiment of the presently disclosed hemodialysis catheter.

FIGS. 5 and 6 illustrate an alternate embodiment of the presently disclosed hemodialysis catheter shown generally as 100. Catheter 100 is substantially the same as catheter 10 but rather than include a scoop or scoops 32, catheter 100 includes guiding structure formed on the distal inner wall defining the side opening 124a for smoothly redirecting blood flow into the arterial lumen 114 of the catheter 100. More specifically, as shown in FIG. 6, catheter 100 includes side opening 124a, which is defined by angled inner walls 140. The distal inner wall 140a (FIG. 6A) defining the side opening 124a defines an acute angle β adjacent the exterior surface 142 of sidewall 120, wherein β is between about 15 degrees and about 75 degrees. In one embodiment, angle β is between about 30 degrees and about 60 degrees. In yet another embodiment, angle β is about 45 degrees.

As illustrated in FIG. 6, catheter 100 includes a diametrically opposed side opening 124b which is configured in a similar fashion as side opening 124a. Thus, each of side openings 124a and 124b include a distal inner wall 140a which defines an acute angle β adjacent the exterior surface 142 of sidewall 120 of catheter 100 which is between about 15 degrees and about 75 degrees. By providing sidewall openings 124a and 124b having a distal inner wall 140a which defines an acute angle β adjacent the exterior surface 142 of sidewall 120 of catheter 100, blood flow can be smoothly directed into either side opening 124a and 124b. Thus, either lumen 114 or 116 can function as the arterial lumen, with minimal flow disruption, minimal platelet activation, and reduced thrombus.

FIG. 7 illustrates an alternate embodiment of the presently disclosed hemodialysis catheter shown generally as 200. Catheter 200 is configured to be non-reversible. As such, side opening 224b is configured, as described above with reference to side openings 124a and 124b (FIG. 6A), to smoothly direct blood flow into arterial lumen 214. In contrast, side opening 224a is configured to smoothly direct blood flow out of the venous lumen 216. As such, the distal inner wall 240a of side opening 224a defines an acute angle adjacent the interior surface 244 of sidewall 220 of between about 15 degrees and about 75 degrees.

FIG. 8 illustrates yet another alternative embodiment of the presently disclosed hemodialysis catheter shown generally as 300. Catheter 300 is substantially identical to catheter 100 in that side opening 324a is identical to side opening 124a. However, side opening 324b is defined by vertical sidewalls 340.

In each of the catheters 100, 200 and 300, the inner proximal wall defining the respective side opening may have an angle which corresponds to the angle of the distal inner wall. Alternatively, the inner proximal wall may have a variety of angular configurations. Although each of catheters 100, 200 and 300 is illustrated to include oval shaped side openings, it is envisioned that the side openings may have a variety of configurations including circular, rectangular, square, or any other polygonal, regular or irregular shape.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A hemodialysis catheter comprising:
a catheter body having a side wall and a septum defining a venous lumen and an arterial lumen, the venous lumen and the arterial lumen each including a distal opening and a side opening formed through the sidewall of the catheter body, each side opening extending from an exterior surface to an interior surface of the side wall, each distal opening and each side opening communicating with a respective venous or arterial lumen, and guiding structure positioned adjacent to a distal end of the side opening communicating with the arterial lumen, the guiding structure including a raised wall extending radially outwardly from a distal wall defining the distal end of the side opening communicating with the arterial lumen and at least partially over the side opening, and terminating in radial and longitudinal spaced relation from a proximal end of the side opening, wherein the guiding structure is configured to redirect blood flow into the arterial lumen through the arterial lumen side opening.

2. The hemodialysis catheter according to claim 1, wherein the raised wall defines a scoop.

3. A catheter for withdrawing fluid from a patient, comprising:
a catheter body defining a first lumen having a side opening spaced from a distal end of the catheter body and communicating with the first lumen, the catheter body including guiding structure positioned adjacent a distal end of the side opening configured to redirect fluid flow into the first lumen through the side opening, the guiding structure including a raised wall extending radially outwardly from a distal wall defining the distal end of the side opening and at partially over the side opening, and terminating in radial and longitudinal spaced relation from a proximal end of the side opening.

4. The catheter according to claim 3, wherein the guiding structure includes an angled distal inner wall defining the side opening which defines an angle θ with the exterior surface of the catheter body, wherein β is between about 15 degrees and about 75 degrees.

5. The catheter according to claim 4, wherein β is between about 30 degrees and about 60 degrees.

* * * * *